(12) United States Patent
Raviv et al.

(10) Patent No.: US 11,363,946 B2
(45) Date of Patent: Jun. 21, 2022

(54) EYE EXAMINATION METHOD AND APPARATUS THEREFOR

(71) Applicant: VirtuOptica Ltd., Karmiel (IL)

(72) Inventors: Ori Raviv, Karmiel (IL); Abraham Sela, Karmiel (IL); Andrey Markus, Karmiel (IL)

(*) Notice: Subject to any disclaimer, the term of this patent is extended or adjusted under 35 U.S.C. 154(b) by 119 days.

(21) Appl. No.: 16/491,167

(22) PCT Filed: May 3, 2018

(86) PCT No.: PCT/IL2018/050251
§ 371 (c)(1),
(2) Date: Sep. 5, 2019

(87) PCT Pub. No.: WO2018/163166
PCT Pub. Date: Sep. 13, 2018

(65) Prior Publication Data
US 2020/0008667 A1    Jan. 9, 2020

Related U.S. Application Data

(60) Provisional application No. 62/581,816, filed on Nov. 6, 2017, provisional application No. 62/507,892, filed
(Continued)

(51) Int. Cl.
*A61B 3/032* (2006.01)
*A61B 3/028* (2006.01)
(Continued)

(52) U.S. Cl.
CPC ............ *A61B 3/032* (2013.01); *A61B 3/0285* (2013.01); *A61B 3/036* (2013.01); *A61B 3/18* (2013.01)

(58) Field of Classification Search
CPC ....... A61B 3/032; A61B 3/0285; A61B 3/036; A61B 3/18; A61B 3/0025; A61B 3/113;
(Continued)

(56) References Cited

U.S. PATENT DOCUMENTS 8,585,609 B2   11/2013  Kiderman et al.
8,824,779 B1*   9/2014  Smyth .................... G06T 7/593
                                                    382/154
(Continued)

FOREIGN PATENT DOCUMENTS

WO    2014/169148 A1    10/2014
WO    2016/001902 A1     1/2016

OTHER PUBLICATIONS

European Search Report; Munich, dated Nov. 10, 2020.

*Primary Examiner* — Mohammed A Hasan
(74) *Attorney, Agent, or Firm* — Patshegen IP; Moshe Pinchas

(57) ABSTRACT

A method for carrying out an eye examination on an examinee is provided. The method includes providing a display configured for displaying a visual stimulus; forming a visual path between the display and at least one eye of the examinee; displaying on the display at least one visual stimulus having visual characteristics; detecting reflexive eye response of the at least one eye in response to the displaying of the visual stimulus; assessing vision of the at least one eye in accordance with the reflexive eye response and the characteristics of the visual stimulus.

20 Claims, 12 Drawing Sheets

Related U.S. Application Data on May 18, 2017, provisional application No. 62/483,424, filed on Apr. 9, 2017, provisional application No. 62/467,144, filed on Mar. 5, 2017.

(51) Int. Cl.
*A61B 3/036* (2006.01)
*A61B 3/18* (2006.01)

(58) Field of Classification Search
CPC ........... A61B 3/028; A61B 3/10; A61B 3/103; G02B 2027/0132; G02B 27/0172; G02C 7/08; G02C 11/10
USPC ......................................... 351/239
See application file for complete search history.

(56) References Cited

U.S. PATENT DOCUMENTS

| | | | |
|---|---|---|---|
| 9,549,669 B2 | 1/2017 | Ofer | |
| 2009/0153796 A1* | 6/2009 | Rabner | A61B 3/028 351/201 |
| 2012/0188512 A1 | 7/2012 | Duston et al. | |
| 2014/0218647 A1 | 8/2014 | Blum et al. | |
| 2014/0253876 A1* | 9/2014 | Klin | A61B 3/0083 351/210 |
| 2014/0362346 A1 | 12/2014 | Leinonen | |
| 2016/0066781 A1* | 3/2016 | Thompson | A61B 3/145 600/476 |
| 2016/0106315 A1* | 4/2016 | Kempinski | A61B 3/113 351/210 |
| 2016/0262608 A1 | 9/2016 | Krueger | |
| 2017/0079523 A1 | 3/2017 | Ofer | |

* cited by examiner

EYE EXAMINATION METHOD AND APPARATUS THEREFOR

FIELD OF INVENTION

The presently disclosed subject matter relates to an eye examination method and apparatus therefor, in general, and in particular to a method and apparatus for performing self-eye examination

BACKGROUND

An eye examination is a series of tests performed by an ophthalmologist (medical doctor), optometrist, or orthoptist assessing vision and ability to focus on and discern objects, as well as other tests and examinations pertaining to the eyes. Health care professionals often recommend that all people should have periodic and thorough eye examinations as part of routine primary care, especially since many eye diseases are asymptomatic.

Currently available eye examination techniques typically consist of a two-stage process, wherein a trained specialist performs an objective eye examination using a Autorefractor and a completely subjective examination using a Phoropter, wherein the examinee is required to perform a quality judgement between pairs of visual stimuli under different visual conditions, set manually by means of a Phoropter.

SUMMARY OF INVENTION

There is provided in accordance with an aspect of the presently disclosed subject matter a method for carrying out an eye examination on an examinee. The method includes providing a display configured for displaying a visual stimulus; forming a visual path between the display and at least one eye of the examinee; displaying on the display at least one visual stimulus having visual characteristics; detecting reflexive eye response of the at least one eye in response to the displaying of the visual stimulus; assessing vision of the at least one eye in accordance with the reflexive eye response and the characteristics of the visual stimulus.

The method can further include determining initial preset values of the optical parameters.

The eye response can be selected from a group including lens tension, pupil size, saccade and eye muscles movement.

The step of displaying the at least one visual stimulus can be carried out after the eye response is below a predetermined threshold.

The method can further include providing at least one adjustable lens assembly and adjusting optical parameters of the adjustable lens assembly after the eye response are detected.

The method can further include displaying a visual stimulus after the step of adjusting the optical parameters. The method can further include displaying a visual stimulus after the step of adjusting the optical parameters.

The method can further include repeatedly adjusting optical parameters of the adjustable lens until the reflexive eye response is below a predetermined threshold, the optical parameters related to correction of at least one vision impairment of the at least one eye, and wherein the step of assessing vision of the at least one eye is in accordance with values of the optical parameters when the reflexive eye response reach the threshold.

The optical parameters can be spherical power. The optical parameters can be cylindrical power. The optical parameters further include cylindrical axis.

The visual stimulus can include an orientation having an axis, and wherein the step of displaying visual stimulus includes displaying the visual stimulus at various orientations and the step of assessing vision includes assessing the axis of the orientation of a visual stimulus for which eye responses were detected.

The characteristics of the visual stimulus can include detectability level.

The step of displaying at least one visual stimulus can include displaying the visual stimulus in varying detectability level and wherein the step of assessing vision includes assessing the detectability level at which the eye response was detected.

The detectability level can include contrast of the visual stimulus with respect to background on the display. The detectability level can include spatial frequency of elements of the visual stimulus.

The step of detecting reflexive eye response can include detecting eye saccade towards the visual stimulus.

The step of displaying at least one visual stimulus can include repeatedly adjusting contrast of the visual stimulus until the eye saccade is detected.

The step displaying at least one visual stimulus can include displaying the stimulus in a randomized location on the display, and the step of detecting can include detecting saccade of the eye towards the randomized location.

The step of displaying at least one visual stimulus can include displaying a series of visual stimuli each of which having an orientation, and wherein the step of assessing vision can include assessing the contrast at which the eye response was detected for each of the visual stimuli.

The visual stimulus can include at least one line and wherein the orientation can be an angle of the line with respect to the horizon.

The series of stimuli can include visual stimulus having at least one angle with respect to the horizon, wherein the angle varies between 0°-180°.

The step of assessing vision can include performing nonlinear regression analysis in which data related to the contrast is modeled by a function characterizing vision impairments. The function can be modeled by calculation of least mean squares of the contrasts for each of the angles.

There is provided in accordance with an aspect of the presently disclosed subject matter an apparatus for performing eye examination on an eye of examinee. The apparatus includes a housing configured to be worn over eyes of a user; a display mounted in the housing and being configured for displaying visual stimuli configured for detecting vision impairment; at least one adjustable lens assembly configured for selectively adjusting optical parameters thereof, the at least one adjustable lens assembly being disposed with respect to the display such that optical path between is adjusted in accordance with the optical parameters; a controller configured for displaying visual stimuli on the display and to adjust the optical parameters assessing thereby the vision impairment.

The optical parameters can be related to correction of at least one vision impairment of the examinee's eye. The optical parameters can be spherical power. The optical parameters can be cylindrical power and cylindrical axis.

The display can be a binocular display, having two displays each of which can be configured to display to one eye of an examinee, and wherein the at least one adjustable lens assembly can include two assemblies each of which being configured to from a visual path between one of the two displays and a respective eye of the examinee.

The at least one adjustable lens assembly can include focus tunable lenses.

The visual stimuli are visual symbols for detecting vision impairments.

The display can be configured with a virtual reality technology for displaying virtual or augmented reality images.

The display can include a lens configured for simulating distanced objects.

The lens can be a virtual reality lens.

The controller can be configured for displaying virtual reality content.

The housing can be virtual reality headset. The lens can be configured to simulate a display disposed at a distance suitable for an eye examination.

The apparatus can further include a detector configured for detecting reflexive eye responses of an eye of an examinee in response to the visual stimulus.

The detector can be an eye tracking device configured to detect eye movements of the eye. The eye tracking device can be configured to detect saccades in response to appearance of a visual stimulus on the display. The eye tracking device can be configured to detect the point of gaze of the examinee.

The display and the at least one adjustable lens assembly are integrated inside an optical module mountable inside the housing.

The module can include an eye tracker for detecting reflexive eye responses of an eye of an examinee.

The module can include a spherical tunable lens and a cylindrical tunable lens. The module can include a virtual reality lens. The virtual reality lens can be disposed between the display and the adjustable lenses assembly. The module can include a cone shaped housing forming thereby a cone of vision between the eye and the display and increasing thereby a field of vision.

The apparatus can further include an input device allowing the examinee to input indication related to the visual stimuli.

The controller can be configured to select a visual stimulus and to adjust the optical parameters in accordance with the indication.

There is provided in accordance with an aspect of the presently disclosed subject matter a system for ordering spectacles. The system includes virtual reality headset having a display and an adjustable lens assembly configured for selectively adjusting optical parameters thereof, the at least one adjustable lens assembly being disposed with respect to the display such that optical path between is adjusted in accordance with the optical parameters; a server having a database of images of eyeglasses frames; an input device configured for selecting a frame from the server; and a controller configured to adjust optical parameters of the adjustable lens assembly to correct vision impairment and to display on the display virtual reality images simulating view through the selected frame with lenses having the optical parameters.

The system can further include a camera configured for capturing images of ambient of the virtual reality headset and wherein the controller is configured to superimposes the images with the virtual reality images, simulating thereby an augmented realty view through the frame.

The optical parameters can include parameters of eye prescription. The optical parameters include multifocal parameters.

The controller can be configured to simulate multifocal field of vision through the frame. The controller can be configured to simulate on the display lens coating having a selected shade.

The system can further include imaging device configured to form a face image of a user wearing the virtual reality headset, superimposing face image together with images of the frame, and displaying same on the display.

The system can further include a gyroscope device configured to detect motion of the user and wherein the controller can be configured to superimposing the face image in accordance with the motion.

The input device can be configured to allow a user to input data related the optical parameters.

The system can further include a communication device coupled to the controller and being configured to transmit images the superimposed face image together to a remote location. The system can further include a communication device coupled to the controller and being configured to transmit images the superimposed face image together to a remote location. The system can further include a communication device coupled to the controller and being configured to transmit information related to the frame and the optical parameters to a remote port begin associated with a laboratory for preparing spectacles. The system can further include a communication device coupled to the controller and allowing a remote control of the optical parameter by a remote port.

BRIEF DESCRIPTION OF THE DRAWINGS

In order to understand the disclosure and to see how it may be carried out in practice, embodiments will now be described, by way of non-limiting examples only, with reference to the accompanying drawings, in which.

DETAILED DESCRIPTION OF EMBODIMENTS

Figure 1:
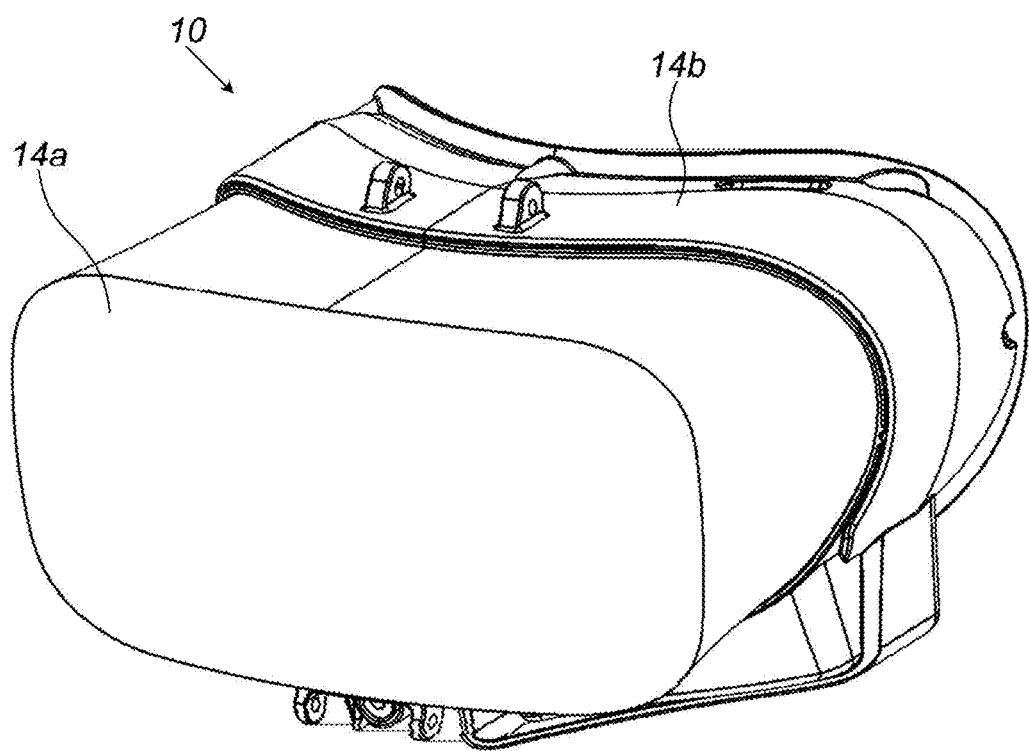
FIG. 1 is a front perspective view of an apparatus for performing eye examination in accordance with an example of the presently disclosed subject matter.

FIG. 1 illustrates an apparatus 10 for performing eye examination in accordance with an example of the presently disclosed subject matter. The apparatus 10 includes a housing 12 configured to be worn over the eyes of a user, similar to a virtual reality headset, and includes an optical casing portion 14a for encasing the optical elements 15 of the apparatus and a face engaging portion 14b for engaging the face of the user such that the view at least one eye of the user is directed inside the optical casing portion 14a.

Figure 2:
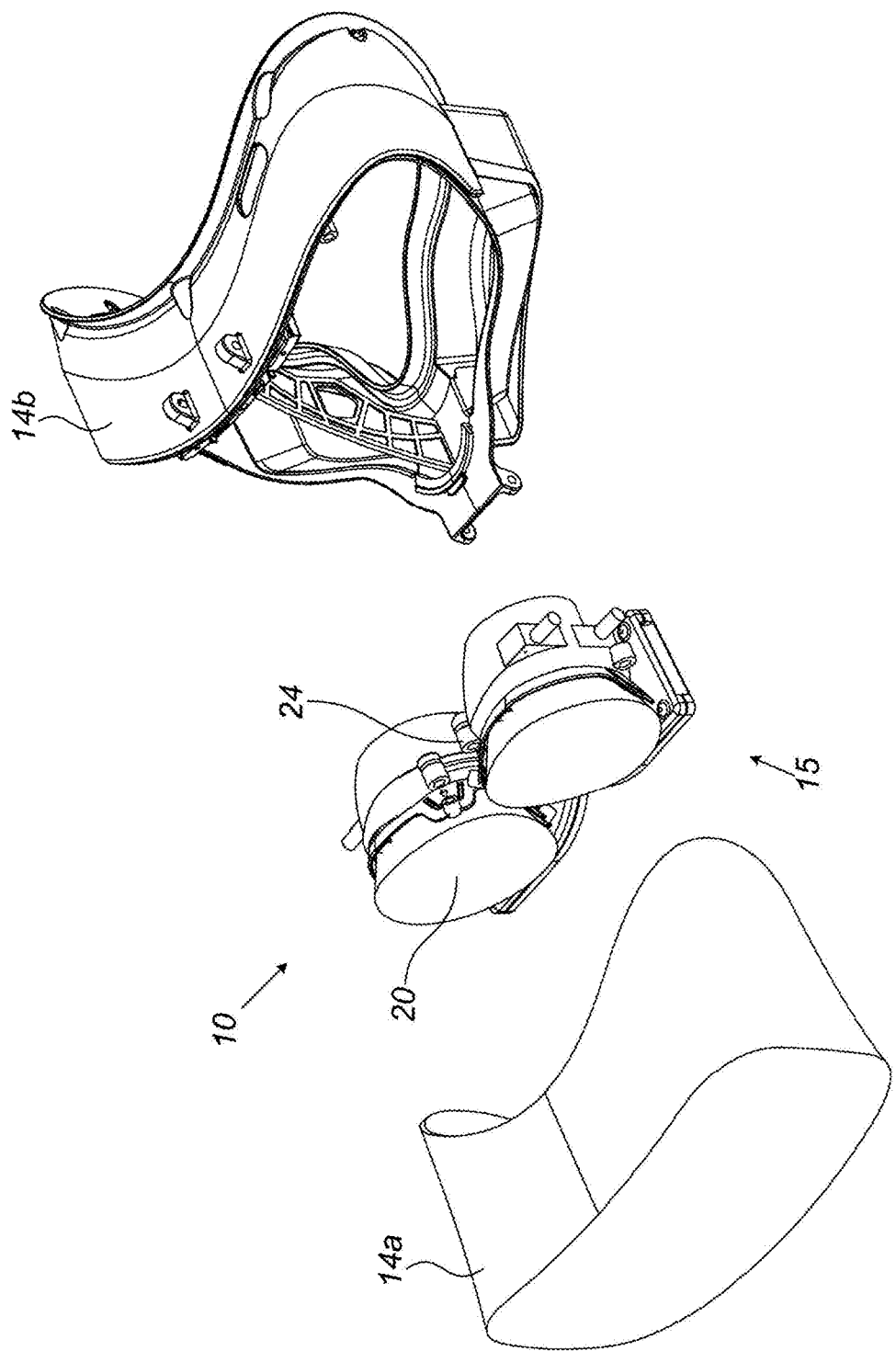
FIG. 2 is an exploded view of the apparatus of FIG. 1.
Figure 3:
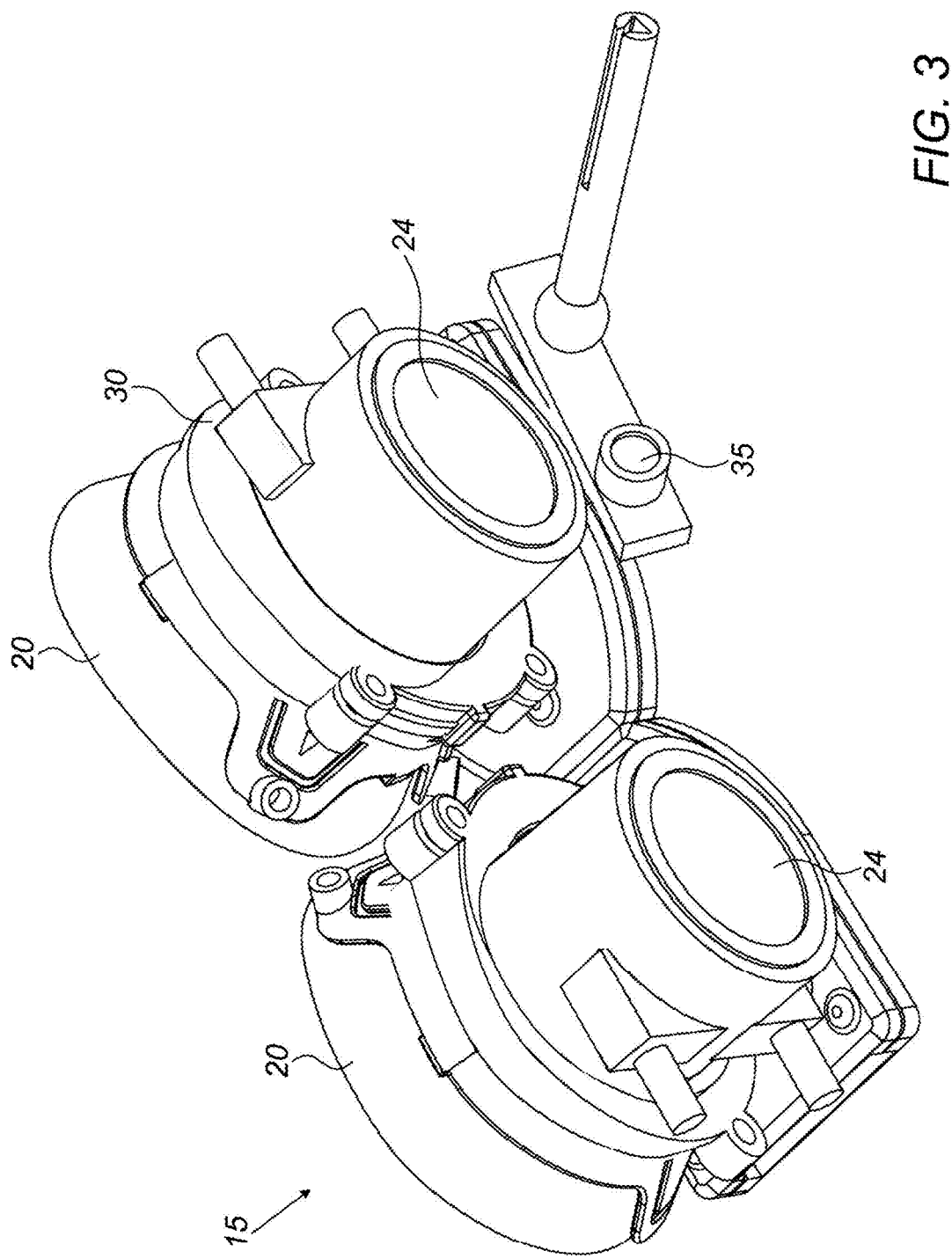
FIG. 3 is a back-perspective view of the lenses assembly of the apparatus of FIG. 1 in accordance with an example of the presently disclosed subject matter.
Figure 4:
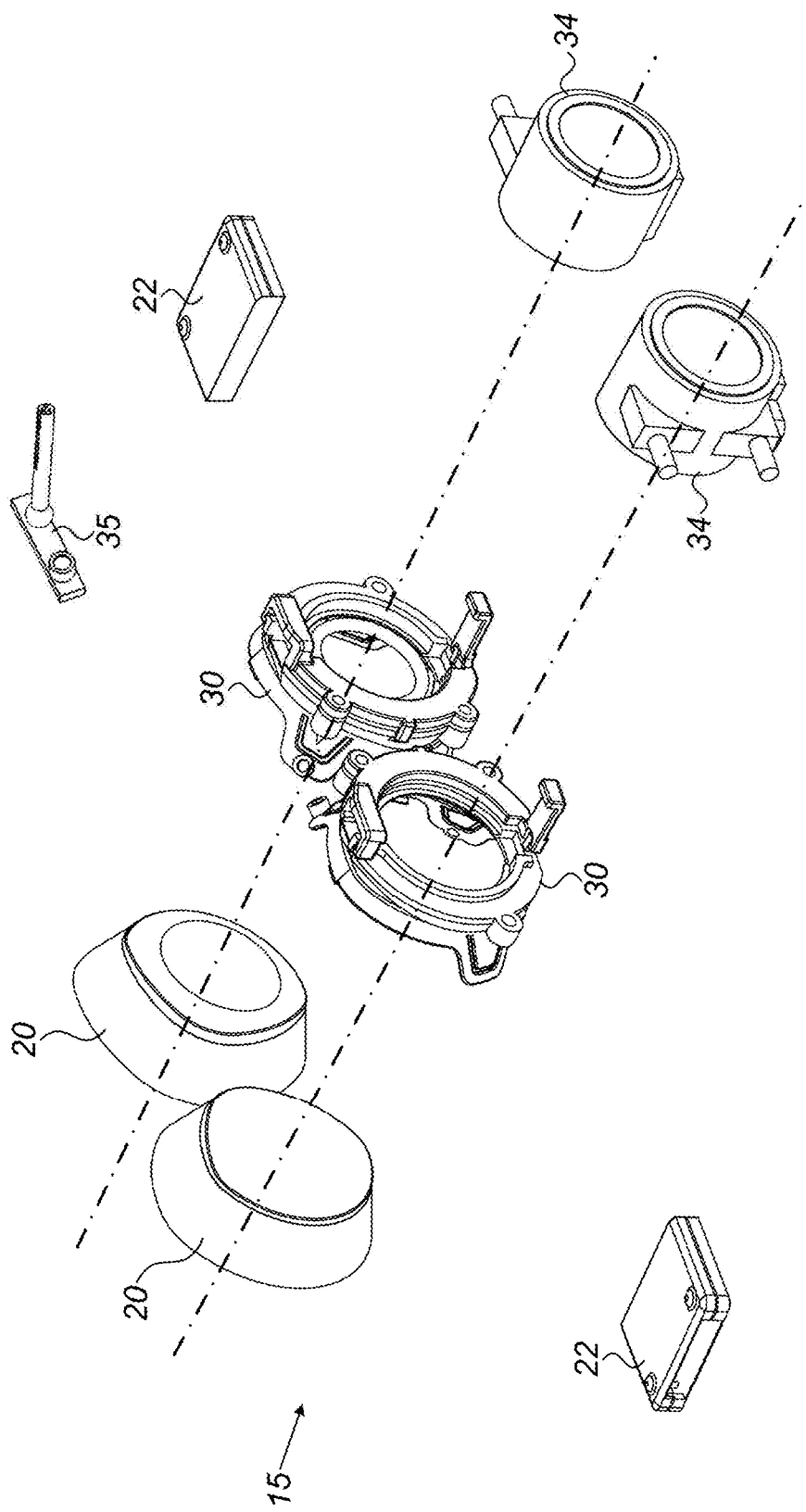
FIG. 4 is an exploded view of the lenses assembly of FIG. 3.

As shown in FIGS. 2-4, the apparatus includes a display 20, and an adjustable lens assembly 24 configured for forming a visual path between the display 20 and at least one eye of the patient. According to the illustrated example the display 20 is a binocular display, having two displays each of which is configured to display to one eye of the user, and the adjustable lens assembly 24 includes two assemblies each of which is configured to from a visual path between one of the displays 20 and the respective eye of the user.

The adjustable lens assembly 24 is configured for selectively adjusting optical parameters thereof, such as focus, and shape etc., and can be configured for correcting vision impairments, such as having a spherical correction component, cylindrical power and axis. The adjustable lens assembly 24 is thus configured for adjusting an optical path between the display and the eye of the user. According to an example, the adjustable lens assembly 24 includes focus tunable lenses which can be either electrically or mechanically actuated such that the optical parameters thereof can be adjusted to provide vision impairment correction.

The apparatus further includes a lens controller 22 for controlling the optical parameters of the adjustable lens assembly 24. In the illustrated case the lens controller 22 includes two controllers for controlling each of the two adjustable lenses separately and independently. As stated above the controller can be configured to adjust the optical parameters of the lenses, such that the lens assembly 24 provides corrections to vision impairments. Accordingly, the controller can be configured to control the power of the lenses in diopter units and to control the curvature of the lens and the axis thereof, such as required for providing cylindrical vision correction.

The apparatus 10 can further include a coupling member 30 for coupling the lens assembly 24 to the display 20. The coupling member 30 according to the illustrated example, is configured to couple each of the lens assembly 24 to the respective display unit 20.

The display 20 incudes a controller 22 configured for displaying a visual stimulus, such as Snellen symbol or other visual symbols for detecting vision impairments. According to an example, the display may be configured with a virtual reality technology for displaying virtual or augmented reality images. Thus, the display 20 can include a virtual reality lens configured for simulating distanced objects. Accordingly, the display 20 can be configured to simulate a Snellen symbol chart disposed in distance, such as 6 m or any other distances suitable for an eye examination. According to an example, the virtual reality lens can be configured for simulating a range of distances, such as a far range for long distance eye examination and close range for simulating eye examination for reading glasses. The display 20 and the controller 22 can be further configure for displaying virtual reality content such as images, movie clips etc., as explained herein below.

According to an example, the apparatus 10 can further include a camera (not shown) configured for capturing images of the surroundings of the user and displaying same on the display 20. According to this example the apparatus 10 the apparatus can be utilized for augmented reality as described herein below.

The apparatus 10 can further include an eye tracking device 35 configured for detecting the point of gaze or other eye movements, such as saccades or microsaccades. As explain hereinbelow the eye tracking device 35 can be utilized for detecting reflexive eye movements (saccades) in response to the appearance of a visual stimulus on the display 20. In addition, the eye tracking device 35 can be utilized for detecting the point of gaze of the examinee such that if the examination includes displaying visual stimulus at randomized locations on the display, the randomized location is at a predetermined distance from the point of gaze.

Figure 5:
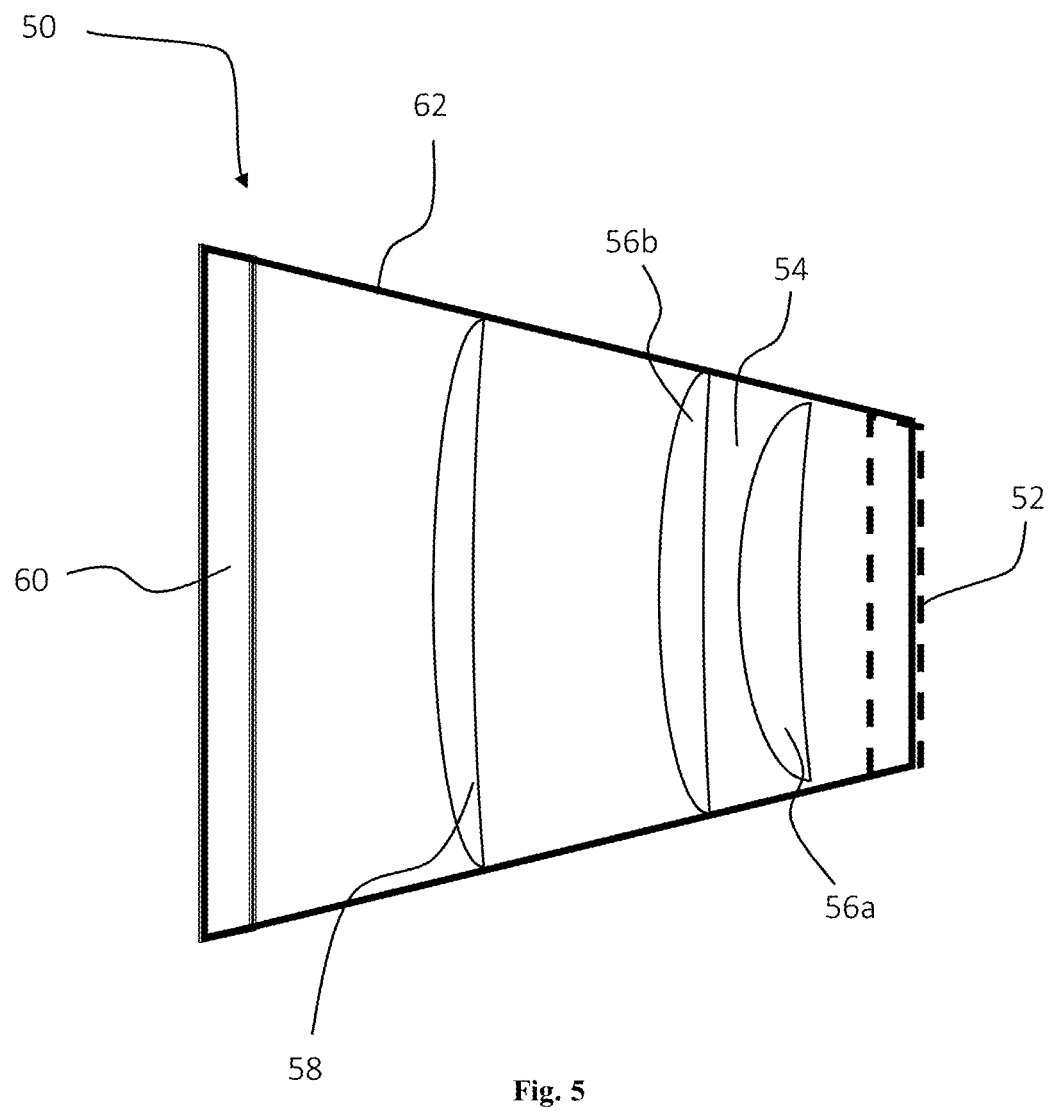
FIG. 5 is a side sectional view of an optical module for mounting in the apparatus of FIG. 1, according to an example of the presently disclosed subject matter.

As shown in FIG. 5, according to an example the apparatus for performing eye examination can include a housing configured to be worn over the eyes of a user, similar to a virtual reality headset and an optical module 50 configured to be mounted inside the housing such for forming a visual path between a display and a single human eye having a single optical axis. The module 50 can include an eye tracker 52 for detecting the point of gaze or other eye movements such as reflexive eye responses in the patient's eye. The eye tracker 52 can further include an LED light ring configured to illuminate the eye, facilitating thereby the detection of the eye movements by the eye tracker.

In addition, the module 50 can include an adjustable lens assembly 54 or other optical mechanism for selectively controlling parameters of the optical path. According to the illustrated example the adjustable lenses assembly 54 includes for example a spherical tunable lens 56a with adaptive spherical correction such that the lens can be adjusted with various degrees of lens power. In addition, the adjustable lenses assembly can include a cylindrical tunable lens 56b configured to adapt various degrees of lens power for astigmatism, at various axes.

The module further includes an integrated display 60, configured for displaying virtual stimulus for performing eye examination and can be further configured for displaying virtual reality content, such as movie clips and games.

Finally, the module 50 includes a virtual reality lens 58 configured to allow the eye to focus on the images displayed on the display 60 so as not to cause near-vision accommodation of the eye's lens. I.e. the virtual reality lens 58 can be configured to simulate image projection from several meters to infinity, i.e. to alter the incoming light from the display in a way that it gets focused on the receptors on the back of the eye. The lens can be configured depending on the distance between the eyes and the display, and can be for example configured to simulate an eye examination chart disposed at a distance of 6 m from the eye of the examinee.

According to the illustrated example, the virtual reality lens 58 is disposed between the display 60 and the adjustable lenses assembly 54, according to other examples however the virtual reality lens 58 can disposed between the eye tracker 52 and the adjustable lenses assembly 54.

The module 50 thus forms an optical path between the display 60 and the eye of the examinee wearing the VR headset, through the virtual reality lens 58 and the adjustable lenses assembly 54. The module 50 is configured such that a first end 51a thereof, is configured to be disposed in close proximity of the human eye, and is sized to allow vision therethrough, while a second end 51b thereof having a wider dimeter than that of the first end 51a, and having the display 60 mounted thereon.

According to the illustrated example the module 50, includes a cone shaped housing 62 or a frustum shaped housing, etc., such that a cone of vision is formed between the eye and the display 60, increasing thereby the field of vision. Accordingly, the diameter of the spherical tunable lens 56a, is slightly smaller than that of the cylindrical tunable lens 56b, since according to the present example the cylindrical tunable lens 56b is disposed closer to the second end 51b.

The module 60, thus provides a single fix optical axis shared between the eye of the examinee wearing the VR headset, the adjustable lenses assembly 54, the virtual reality lens 58 and the display 60. Accordingly, the module 60 provides a stable visual path between the display and the eye.

The module 60 can be incorporated inside an apparatus for carrying out an eye examination (not shown). The apparatus can be provided with two modules, one for each eye. The modules 60 can be replaceable, such that the apparatus can be provided with a plurality of modules each configured with certain parameters such as size, kind of adjustable lenses assembly, and other parameters required for performing the eye examination.

The apparatus can thus be used for performing the measurements related to refractive errors of the patient's eye; and adjusting adjustable lenses assembly to accurately correct the refractive errors in accordance with the reflexive eye responses. In addition, the apparatus can be in augmented reality glasses, such that the glasses provided the virtual reality component together with the corrections of the refractive errors of the user's eye, as described here in below.

In addition, as described here in below, the module can be utilized in a device configured to allow users to experience an eyeglasses prescription, i.e. to provide the user with a simulation of wearing corrective eyeglasses, which have refractive errors in accordance with a predetermined prescription. Finally, the module can be used in an autorefractor apparatus.

According to an aspect of the presently disclosed subject matter there is provided a method for performing an eyesight examination including measuring the reflexive responses of the eye in response to visual stimulation. The method can be implemented with a display device configured to display various visual stimulations, such as an electronic display. In addition, the method according to an example can be carried out with an adjustable lenses assembly configured to adjust an optical path between the eye of the examinee and the display, such as tunable lenses, collimators, or other devices.

As explained herein above the adjustable lenses assembly can be configured for selectively controlling parameters of the optical path, such that the lens can be adjusted with various degrees of lens power and cylindrical power at various axes.

Finally, according to an example the method further requires a sensor configured for measuring eye reflexes, such as an eye tracker for detecting gaze movements (fixations, saccades, etc.), a sensor for detecting accommodation response and/or changes of the pupil's size.

Figure 6:
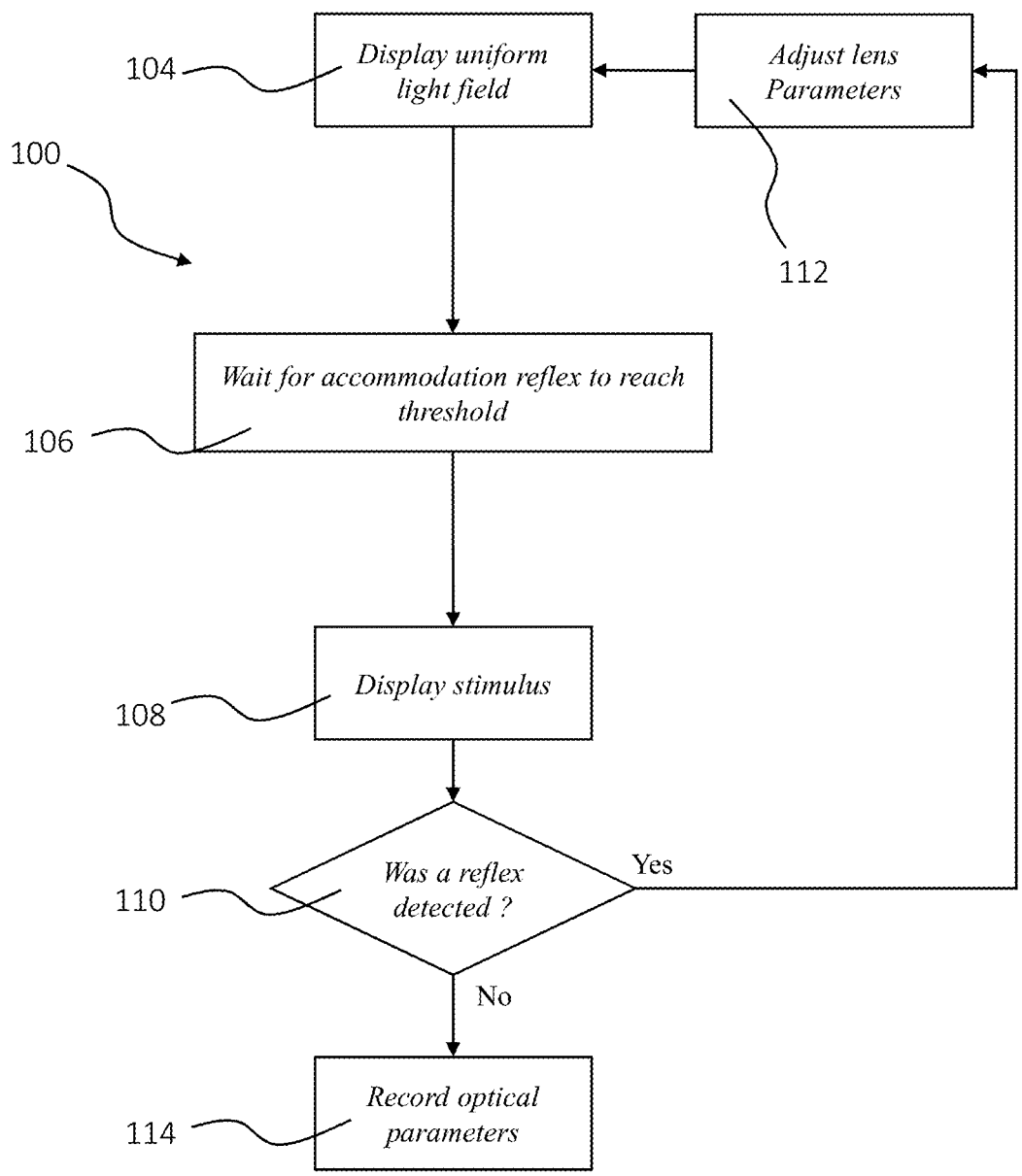
FIG. 6 is a flow chart diagram illustrating a method for automatic eye examination in accordance with an example of the presently disclosed subject matter.

With reference to FIG. 6, according to an example the method 100 for performing an eye-sight examination is configured to measure the required spherical correction. The method relies on adjusting the optical path between the display and the eye lens until the eye reflexes are stopped or at least reduced.

Firstly, initial preset values of the adjustable lenses assembly are selected (block 102), i.e., in a case of a tunable lenses the lenses are configured with a certain spherical power. The initial preset values can be determined either arbitrarily, or by presenting a stimulus at a central location and adjusting the spherical power until the examinee indicates that a comfort zone has been reached. According to an example, a controller can be utilized for allowing the examinee to adjust the spherical power such that he/she reaches the comfort zone in which the stimulus can be seen relatively well.

In addition, at the initial stage the display is set up to present a uniform blank light field (block 104), so as to allow the eye to accommodate to its default state. At this point, the eye lens is expected to remain flexed and the pupil is expected to dilate according to the amount of light emitted from the display and which reaches the eye. The eye responses such as changes in the eye's lens tension and/or pupil size, caused by accommodation to the displayed stimulus, can be detected by a sensor as stated above. Accordingly, at this stage of the examination, the examinee is given time for the accommodation to occur until the his/her eye reflexes stop or at least reduced below a certain threshold (block 106).

Once accommodation occurs and the eye reflexes stop or at least reduced below a certain threshold, a stimulus is presented on the display such that it is visible through the optical path (block 108). In order to preclude pupil size changes due to change in the overall amount of light that reaches the eye, the average luminance of the screen is preferably maintained substantially constant. Measurement of the accommodation reflex of the eye (block 110) is simultaneously taken continuously for the duration of the presentation or until a time-out occurs. In case accommodation reflex are detected the optical path is adjusted by adjusting the lens parameters (block 112), such as increasing or decreasing spherical power. Following the adjusting of the adjusting the lens parameters steps of waiting until eye reflexes stop (block 106), displaying a stimulus (block 108) and measurement of the accommodation reflex of the eye (block 110) are repeated until the accommodation reflex level falls below a predetermined threshold.

When the latter occurs the optical parameters of the lens with which no accommodation reflex were detected are assumed to be the required optical parameter to correct vision impairments of the examinee, thus these optical parameters are recorded as the result of the examination (block 114).

It is appreciated that the accommodation reflexes measurements are time-locked to the stimulation, thereby constituting a response detection mechanism intended to measure reflexive responses to the onset of visual stimulation of the eye under preset conditions.

In addition, it is appreciated that once the optical parameters for which no accommodation reflexes were detected, the optical parameters are changed back to the previous values to ensure that the corrected values are detected. This step can be repeated a predetermined amount of times, with "stepladder" algorithm, i.e. selecting back and forth between two adjacent values of the optical parameters to verify that when a first value is selected reflexes are detected whereas when a second value is selected no reflexes are detected. For example, if after five or ten iterations, for a first value of the optical parameters reflexes are detected while for a second value of the optical parameters no reflexes are detected, it can be concluded that the required values of the optical parameters are the first values, or a third value between the first and second values.

In cases when lens adjustment is insufficiently fine-grained, extrapolation of the values obtained through this method can be used to further increase accuracy. I.e. if for example the difference between the first and second values of the optical parameters is a full diopter, and it is suspected that the required value of the optical parameter is a third value between the first and second values, the method can be performed with increasing the optical parameter by half of a diopter or a quarter of a diopter.

It is appreciated that several specific methods may be applied for the accommodation reflex measurement, either individually or in combination. Additionally, several types of eye reflexes, such as pupil size change, lens accommodation, gaze shifts (saccades) and others can be used.

In addition, a similar examination method can be applied for finding cylinder axis and cylindrical power. The overall principle is identical to that described above with reference to FIG. 6. According to an example, once the required spherical correction is determined, the optical parameters of the lens are maintained at the same spherical power, and the visual stimulus presented on the display are configured to detect cylinder axis and/or cylindrical power. In addition, the adjustment of the lens parameters can include adjusting the cylinder axis and/or cylindrical power in response to detection of accommodation reflexes. According to an example the cylindrical axis can be detected by displaying a visual stimulus at an orientation having a certain axis, such as lines disposed along a predetermined axis. When accommodation reflexes are detected, the axis of the visual stimulus at which the reflexes are detected is recorded and the cylindrical axis is determined as the line perpendicular to a line connecting between the detected point and the center of the visual field.

Since the cylindrical axis is an axis along which additional correction is required on top of the spherical correction, the cylindrical power must be determined as well. In order to determine the cylindrical power, a visual stimulus is displayed with an orientation along the detected axis and the lens are adjusted such that the cylindrical power along the axis is adjusted until no accommodation reflexes are detected.

It is appreciated that the above method for performing an eye-sight examination can be carried out by apparatus 10 described with reference to FIGS. 1-4, alternatively the method can be implemented with a regular eye chart and regular phoropter allowing manual or automatic adjustment of the optical parameters of the lenses thereof. In case the apparatus 10 described with reference to FIGS. 1-4 is utilized the examination can be a fully automated examination and the display controller 22 together with the lenses controller 22 can be configured to carried out the examination in accordance with the data received from the eye tracking device 35.

Figure 7:
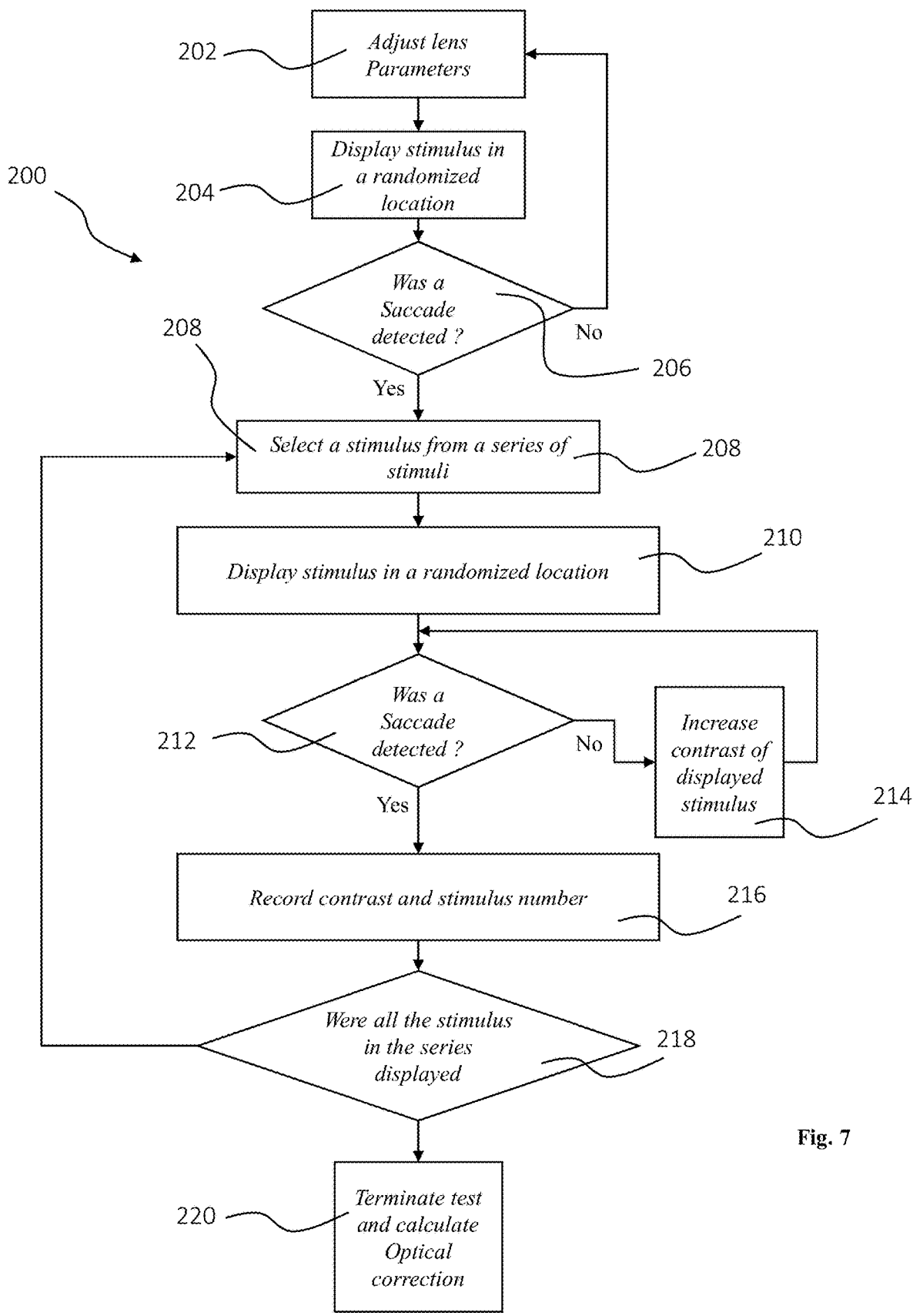
FIG. 7 is a flow chart diagram illustrating a method for automatic eye examination in accordance with another example of the presently disclosed subject matter.

FIG. 7 illustrates another example of a method 200 for performing an eye-sight examination is configured to measure the required vision correction. According to this example, the eye examination is performed by displaying a series of stimulus in varying contrasts and detecting for each stimulus the contrast at which the stimulus was visible to the examinee Detecting the contrast at which the stimulus was visible can be carried out by displaying the stimulus in randomized locations on the display and utilizing an eye tracker configured to track saccades of the eye in the direction of the displayed stimulus. In accordance with the contrast at which the saccade was detected the required optical correction can be calculated as described herein below.

According to the illustrated example, at the initial stage the examinee is tested to determine the required basic spherical correction, so the examinee can view the stimulus on the display. To that end the lens parameters are adjusted to an estimated required value (block 202), and a stimulus is displayed on a randomized location (block 204). If a saccade was not detected by the eye tracker (block 206), the lens parameters are further adjusted to provide a better optical correction, until the eye of the examinee is able to view the stimulus. Once the required lens parameters are detected, the exact required vision correction can be detected, by displaying a series of stimuli at randomized locations on the display. The series of stimuli can include various forms or shapes configured for detecting the visual acuity of the human eye and can be configured to detect spherical as well as cylindrical impairment.

Figure 8C:
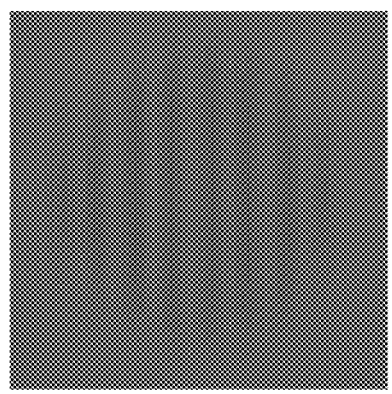
FIGS. 8A-8C are a series of visual stimulus for an eye examination in accordance with an example of the of the presently disclosed subject matter.
Figure 8B:
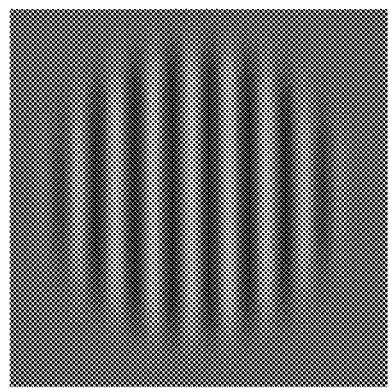
Figure 8A:
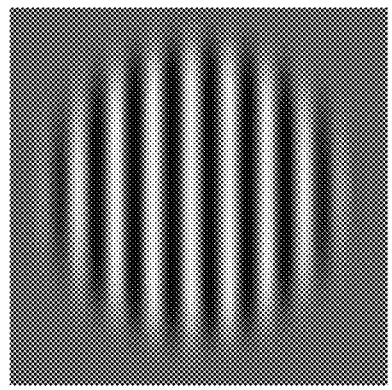

According to an example, the stimuli include series of stimulus with carrying orientations. For example, the stimulus can include parallel lines extending at a certain axis with respect to the horizon, such as shown in FIGS. 8A-8C. According to these examples the lines are displayed at various angles with respect to the horizon. For example, the series can include similar stimulus of lines in which, each of the stimulus has lines disposed at a different angle. For example, the series can include stimuli with lines disposed at exes between 0°-180° with a delta of 10°, i.e. at 10°, 20°, 30° with respect to the horizon, etc. This allows detecting the visual acuity of the examinee at various angles of the eye, i.e. the cylindrical impairment. According to an example, each stimulus in the series can be repeated three times in the series so as to preclude errors. It is appreciated that the order of the stimulus presentation in the series is randomized, so as to avoid expectation effects by the examinee. I.e., the entire stimulation series is created in advance in terms of the number of repetitions of each axis tilt angle, and then randomized in terms of the order at which each stimulus is presented and the presentation location.

Accordingly, one of the stimulus in the series is selected (block 208) and is displayed on a randomized location on the display (block 210). It is appreciated that the randomized location is configured so as to mitigate the learning effect, i.e. after a few displays of stimuli, the examinee will direct his/her eye to the location where the next stimulus is expected to be presented. Accordingly, the examinee is instructed to generally focus his view at the center of the display while the stimuli are displayed in various randomized locations on the display, causing an involuntary eye movement towards the stimulus. If indeed the stimulus is detected by the eye, a saccade is detected, for example by an eye tracker (block 212). In case no saccade is detected, it is assumed that the eye of the examinee did not detect the stimulus due to the low contrast level. Thus, if no saccade is detected the contrast of the stimulus is slightly increased (block 214) allowing the stimulus to be detected by the eye of the examinee. As shown in FIGS. 8A to 8C, at this stage the stimulus forms and orientation is not changed, and only the contrast is increased from example from the contrast shown in FIG. 8a to the contrast shown in FIG. 8B. This step is repeated until the saccade is detected (block 212), i.e. the examinee's eye detects the stimulus.

Once a saccade is detected the contrast at which the saccade's onset is detected is recorded together with the stimulus number in the series (block 216) and is stored for later calculation.

Next, if there are more stimulus in the series which were not yet displayed (block 218), the process is repeated for the next stimulus in the series (block 208). As explained herein above the next stimulus in the series can have a different or same orientation, e.g. lines extending at a different angle with respect to the angles of the lines of the previous stimulus. As for the previous stimulus, the next stimulus is displayed in a randomized location on the display (block 210) and is displayed with a relatively low contrast which is gradually increased (block 214) until saccade are detected (block 212).

Once the series is completed, i.e. all the stimulus in the series were displayed (block 216), the test is terminated, and the required optical correction is calculated (block 2202) in accordance with the contrast at which each stimulus is detected.

Figure 9A:
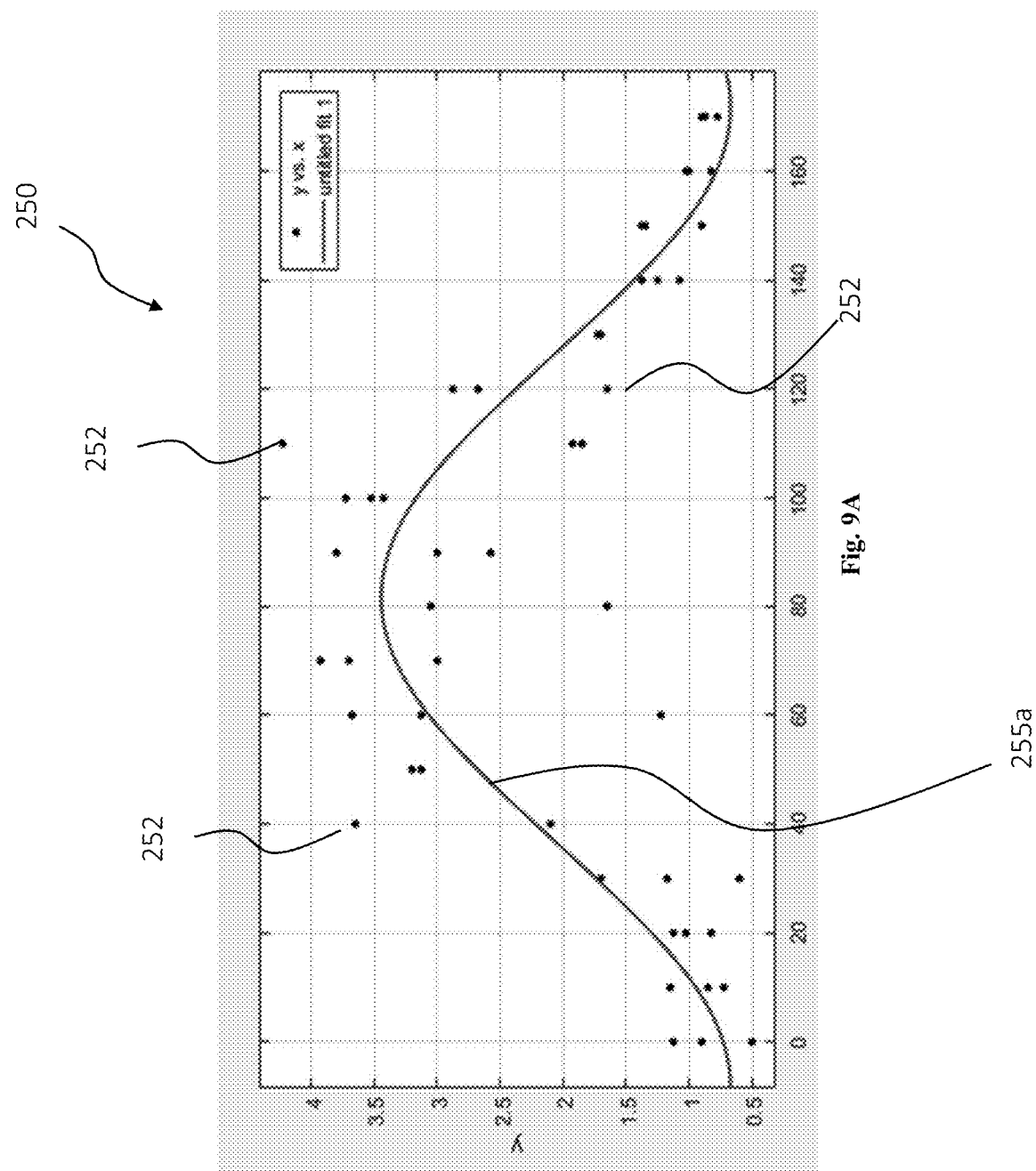
FIGS. 9A-9B are graph representations of an eye examination results carried out in accordance with the method of FIG. 7.

As shown in the graph 250 illustrated in FIG. 9A, the test results can be represented on a graph in which the contrast level is denoted on the Y axis while the angle of the stimulus orientation is denoted on the X axis. The dots 252 in the graph are the contrast level of each stimulus at which saccade was detected.

In order to extract the required optical parameters from the above graph, statistical tools can be utilized such as nonlinear regression analysis in which the data is modeled by a function which is a nonlinear combination of the model parameters and depends on one or more independent variables.

According to an example, the function by which the data is modeled can be:

$$z = s + c \cdot \cos(2 \cdot (a+x))$$

wherein z and x are the variables measured for each stimulus during the test, i.e. z is the detected contrast for each stimulus, and x is the orientation angle of the of the stimulus, i.e. the angel of the lines of each stimulus with respect to the horizon.

The independent variables of the above function are s which represent the required spherical parameter; c is the cylinder parameter; and a represent the cylinder axis (degrees). The nonlinear regression analysis according to the illustrated graph utilizes calculation of least mean squares, i.e. the curve 255a illustrated on the graph is formed of values which represent the least mean square of the dots 252 representing the results of the eye examination. Since the above function is cosinusoidal function, the curve 255a has a cosinusoidal from. Since astigmatism is axis dependent, i.e. for each axis of the cornea different lens power is required, this vision impairment can be represented as a sinus function. The result of this nonlinear regression analysis yields the independent spherical parameter s, the cylinder parameter c and the cylinder axis a.

Figure 9B:
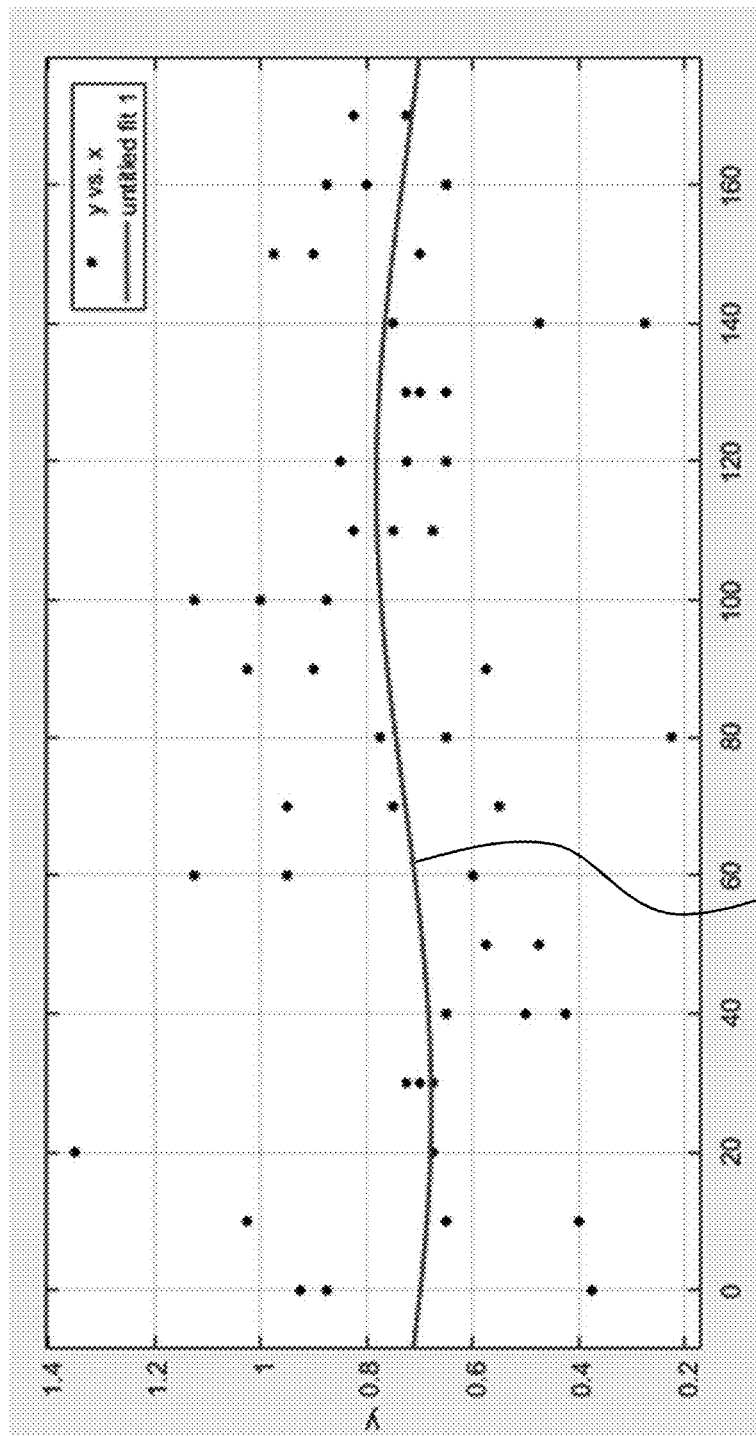
Figure 10C:
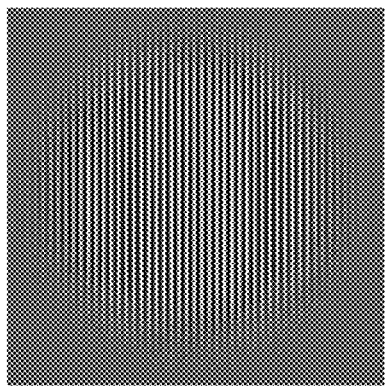
FIGS. 10A-10C are a series of visual stimulus for an eye examination in accordance with another example of the of the presently disclosed subject matter.
Figure 10B:
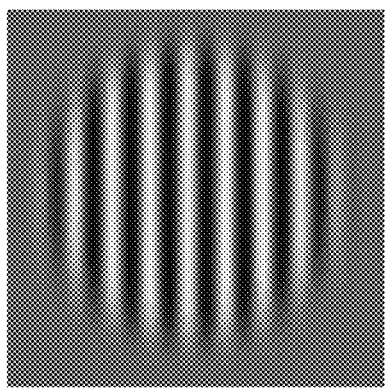
Figure 10A:
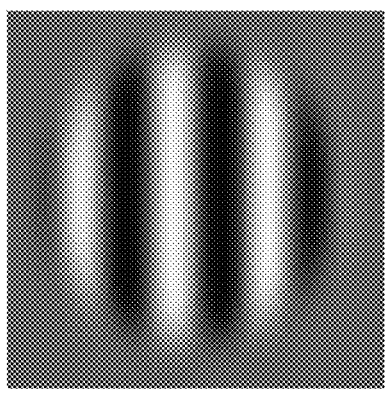

The changes in the curvature of the graph represent the astigmatism of the examinee, while the baseline represent the required spherical correction of the examinee. As shown in FIG. 9B, for another examinee, the result can yield a graph which as a mild cosinusoidal curvature 255b, i.e. very minimal astigmatism is detected.

According to another example, the above function can be slightly amended as follows:

$$z = s + c \cdot \cos(2 \cdot (a+x)) + b \cdot y$$

Wherein y is the number of stimulus in the series, and b is an auxiliary coefficient representing the effect of the duration of the examination. That is to say, according to an example, at the initial stages of the examination the examinee might be distracted by various factors causing delays in detecting the stimulus or lack of ability to correctly focus on the display, thus the results of the stimulus detection of the first stimuli in the series might not be accurate. Additionally, as the examination proceeds the eye of the examinee might get tired such that the stimulus at the end of the series are not properly detected by the eye. Accordingly, the y parameter representing the number of the stimulus in the series can be factored by coefficient b so as mitigate these effects.

Reference is now made to FIGS. 9A-9C, according to another example the stimuli can be lines representation similar to that of FIGS. 8A-8C, however with changing spatial frequency, i.e. for each displayed stimulus the contrast of the stimulus is constant, while the spatial frequency is decreased during the eye examination until saccade is detected. As in the example of FIGS. 8A-8C the series of stimuli include a plurality of stimulus with lines have varying orientations, i.e. the angle of the lines changes such that the lines are disposed at angles between 0°-180° with a delta of 10° with respect to the horizon, etc.

Figure 11:
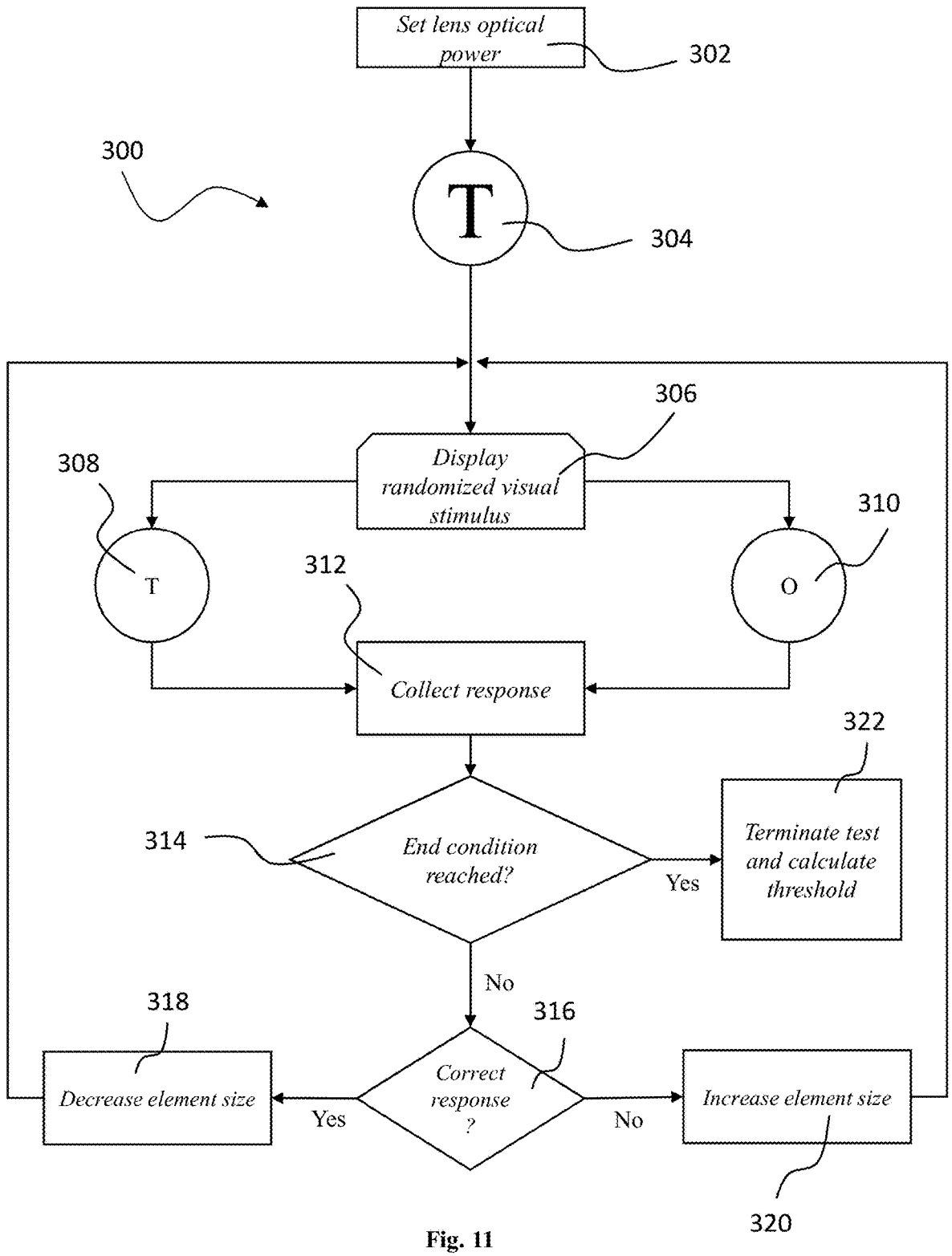
FIG. 11 is a flow chart diagram illustrating a method for self-eye examination in accordance with another example of the presently disclosed subject matter.

Reference is now made to FIG. 11, illustrating a method for performing an eye examination according to another example of the presently disclosed subject matter. According to this example, the eye examination is performed in accordance with subjective responses of the examinee, i.e. contrary to the method of FIGS. 6 and 7 in which the eye examination included detecting subjective responses of the eye by assessing involuntary eye movement, according to the present example the examination includes receiving responses from the examinee regarding his/her ability to view the stimulus.

The method can be carried out with a system having a display an adjustable lens assembly, which can be an automatic or manual assembly. The system can further include a response device allowing the user to input his/her response to the visual stimulus, as explained hereinbelow. According to the example the method can be carried out with an apparatus similar to that which is described in the FIG. 1-4. I.e., a wearable apparatus having a housing similar to a virtual reality headset and including a display and an adjustable lens assembly configured for forming a visual path between the display and at least one eye of the examinee. The display can include a virtual reality lens stimulating a distance of 6 m between the eye and the display. Finally, the apparatus according to the present example includes an input device, allowing the examinee to input his/her response to the visual stimulus, such as a game controller or any other input device.

The method, as illustrated in FIG. 11 makes use of methods known from the field of psychophysical research and the field of signal detection theory as applied to humans. The method aims at detecting the lowest detectable threshold of a visual signal under given visual conditions, set by the lens assembly, in a rapid series of repetitive signal presentation.

According to the example illustrated in FIG. 11, the lens assembly is set with certain values of the optical parameters (block 302), i.e., in a case of a tunable lenses the lenses are configured with a certain spherical power. The initial preset values can be determined either arbitrarily, or in accordance with previous prescription of the examinee According to an example, a controller can be utilized for allowing the examinee to adjust the spherical power such that he/she reaches the comfort zone in which the stimulus can be seen relatively well.

A visual stimulus is displayed on the display (block 304), at an initial size, such that the examinee is able to recognize the stimulus. According to the illustrated example, the stimulus is the letter T, according to other examples the visual stimulus can be a letter or an image.

A randomized visual stimulus is then displayed on the display (block 306), which can be either the same visual stimulus as displayed in the initial step (block 304), or a different stimulus, here illustrated as a different letter O. The examinee is then prompted to indicate if the visual stimulus is the same as that which was displayed at the initial stage (block 308) or not (block 310).

The examinee's input is collected (block 312) and stored in a data set to be analyzed. According to an example, the step of displaying randomized visual stimulus is repeated until a predetermined end condition is reached (block 314). An example of an end condition is discussed herein below. If that end condition is not yet reached the examination proceeds, and if the examinee provided the correct answer regarding the visual stimulus (block 316), the size of the visual stimulus is decreased (block 318). In other words, if the visual stimulus displayed during the previous step (block 306) is the same as the visual stimulus displayed at the initial stage (block 304), and the examinee correctly identified that it is the same stimulus then the visual stimulus is decreased (block 318), so as to further challenge the examinee with a smaller size stimulus. Similarly, if the visual stimulus displayed during the previous step (block 306) is not the same as the visual stimulus displayed at the initial stage (block 304), and the examinee correctly identified that it is not the same stimulus then the size of the visual stimulus is decreased (block 318), so as to further challenge the examinee with a smaller size stimulus.

If on the other hand the examinee's input is found to be wrong, i.e. then the size of the visual stimulus is increased (block 320).

Once the size of the next visual stimulus is determined, a randomized visual stimulus is displayed again (block 306), this time at the selected size. The examinee is again prompted to indicate if the visual stimulus is the same as that which was displayed at the initial stage (block 308) or not (block 310).

Once again, if in accordance with the examinee's input the size of the next visual stimulus is either decreased or increased. This way, a threshold in which the examinee is no longer able to detect the displayed stimulus is reached. This threshold can be defined as the size at which the examinee is no longer able to detect the displayed stimulus a predetermined amount of repetitions, at which point the examination can be terminated (block 322), or the optical parameters can be modified. Alternatively, the end condition (block 314), at which the examination is terminated can be a predetermined number of iterations in which the examinee's responses are alternately correct and incorrect, i.e. for a visual stimulus of a first size the examinee is able to detect the stimulus and for a stimulus of a second size, slightly smaller than the first size the examinee is unable to detect the visual stimulus. This way, it can be ascertained that the threshold is any size between the first size and the second size. At this point the examination is terminates (block 322), and the threshold for the optical parameters of the lens are recorded.

The above method can be repeated for other optical parameters and the above threshold can be compared to threshold under adjacent lens settings. The optimal lens setting is then used as the basis for the produced prescription. In cases when lens adjustment is insufficiently fine-grained (typically, optical power increments greater than 0.25 diopter), extrapolation of the function linking the acuity threshold with the set optical power may be used to further increase accuracy.

It is appreciated that a similar method can be carried out for evaluating spherical and cylindrical correction axis. For detecting cylindrical axis, the visual stimulus can be disposed at various orientations and can be selected such that for certain orientations the visual stimulus visibility depends on the cylindrical axis of the examinee's eye. An example of such stimulus is shown in FIGS. 8A-8C and FIGS. 10A to 10C.

When cylindrical axis is evaluated, at each iteration, instead of changing the optical power of the lens assembly, the cylindrical axis of there is changed, or the orientation of the visual stimulus.

Accordingly, the above method allows user to carry out self eye-examination, with an apparatus such as the apparatus 10 of FIGS. 1-4. The apparatus can include a CPU configured to carry out the above method. It is noted that according to the method of FIG. 11, the method is carried out in accordance with input of the examinee and not in accordance with eye responses, as in the method of FIG. 6 or 7. Accordingly, the apparatus, may be configured without an eye tracker, however with an input device, such as a game controller configured to allow the examinee to indicate his/her detection of the visual stimuli.

There is provided in accordance with another aspect of the presently disclosed subject matter a system for ordering spectacles. The system can be integrated with the apparatus of FIG. 1-4 allowing thereby performing eye examination. As indicated with reference to the methods for performing eye examination illustrated in FIGS. 6 and 7 the apparatus may include an eye responses detector, such as an eye tracker. Alternatively, as indicated with reference to the method for performing eye examination illustrated in FIG. 11 the apparatus may include an input device allowing the user to indicate his/her detection of visual stimuli.

The system further includes a computerized controller, such as a PC or a microcontroller-based device, for controlling the operation of the lenses and the images displayed on the display, and a power source, such as a battery.

The system can be configured for adjusting the lenses to correct the refractive errors in accordance with the reflexive eye responses as described in FIG. 6 or 7, and/or in accordance with subjective responses inputted by the examinee as described in FIG. 11. The display according to this example is configured to display to the user images and characters for an eye examination in accordance with the reflexive eye responses.

The system can further include a controller allowing the user to directly control the parameters of the lenses, such that the lenses compensate for visual defects in the user's vision. The response controller can be further configured to allow the user to control the display, for example, the kind and the size of the images displayed thereon.

According to an example the system can be configured to allow an eye examination with a computer game displaying various images and urging the user to provide his/her input regarding the images. The eye examination can be carried out in accordance with the user's input throughout the game and in accordance with reflexive eye responses.

The system can be further configured with augmented reality capabilities, such that the user can have a view of physical, real-world environment augmented by visual elements displayed on the display. The visual elements can be images allowing the user to test the optical prescription obtain by the eye examination without actually wearing glasses. The apparatus can be a wearable device allowing the user to walk around and test the comfort of the eyes with the optical prescription.

The apparatus can be in a form of a helmet or a virtual realty headset having an eye cover such that the user wears the helmet to perform the eye examination and spectacles order. According to an example the system can be configured with virtual reality capabilities, such that the user can test the comfort of the prescription in a fully virtual reality.

Furthermore, the system allows for multifocal adjustment by allowing the user to experience the use of the prescription for viewing close objects and distanced objects. The system can allow the user to control the regions on the ordered lenses in accordance with his/her real time experience. According to an example the system can be configured for adjusting the lenses such that the optical parameters thereof are similar to those of multifocal lenses.

Alternatively, the system can be configured to determine a first region of the lens intended for near vision correction and a second region of the lens intended for distant vision correction. The system can further be configured to track the point of gaze of the user such that when the user's gaze is directed through the first region, areas on the display corresponding to the second region appear to be blurry. Similarly, when the user's gaze is directed through the second region, areas on the display corresponding to the first region appear to be blurry. This way, the user can experience a simulation of a multifocal eyeglasses and can adjust the size and orientation of each region until a comfort zone is reached.

In addition, the system allows the user to select the desired coating by experiencing the use of the selected coating in virtual reality. According to an example the display is configured to show a selection of coating types and colors and/or coating parameters such as shade etc. The image of the display is then modified to form an imaging of the various environments with the use of lenses having the selected coating. The user can thus experience the combination of the lenses with the selected prescription and the selected coating.

In addition, the system can be configured to measure interpupil distance by using an eye tracker detecting the location of each of the eyes. Alternatively, if the system includes two optical modules having a display and a visual-paths between each of the user's eyes and the display, the system can be equipped with a mechanical arrangement for controlling disposition of the modules. I.e., the user when using two eyes may experience to circles of his field of vision one for each eye. The mechanical arrangement, as used in virtual reality headsets, allows controlling the disposition of the two modules until the two circles coincide. The distance between the center of the two displays can be calculated as the interpupil distance.

In addition, the system can be configured to perform Color Blindness Test by displaying various colors and shades on the display.

According to a further example, the system is further configured for selection of glasses frames and viewing a virtual reality of himself wearing the glasses with the selected frame. That is to say, the system can be configured to allow the user to experience the field of view while wearing the selected frame. The latter can be carried out by providing cameras capturing the ambient of the user and displaying same on the display. Thus, the system can display images reflecting the images which are seen via the selected frame. In addition, the system can be configured to provide the user with an image of himself wearing the selected frame by displaying a virtual mirror i.e. imaging device for imaging the face of the user and adding a selected frame and lenses to the user's image.

Furthermore, the virtual capabilities of the system can be configured to allow the user to move his/her head in various direction while an image of the user is displayed on the display simulating a view in the mirror. This way, the user can select a frame and virtually experience his look while wearing the frame. The system can thus include a gyroscope device, or similar devices configured to detect motion of the user's head. This way, the user can move his head in various directions and the user's image displayed on the display is modified in accordance with the user's head movements.

Furthermore, the system can be configured to allow the user to obtain virtual images of himself wearing glasses with a selected frame and to send these image to remote devices. For example, the user can share these images via social networks such as Facebook WhatsApp etc. in addition, the system can be configured to allow the user to receive feedback from remote users regarding the frame selection. For example, the user can send an image of himself wearing the glasses with the selected frame and request feedback from a friend regarding the selected frame.

According to an example of the invention the system is further configured to send the eyeglass prescription to a remote location where an authorized person can verify and approve the prescription, such as an optometrist or a medical doctor. The system can be further configured to allow the remote authorized person to communicate with the user to discuss the prescription and possibilities for vision correction. The communication can be initiated by the user or by the authorized person can be carried out via a video or audio conversation, such as a Voice over IP, or via text messages displayed on the display. This way, the system allows user at a remote location to consult with a professional person which might otherwise not be accessible for the remote user.

According to a further example, the system can be configured to allow the remote authorized person to control the system, such as controlling the lenses, and/or the images displayed on the display. It is appreciated that remote controlling of the system can be carried out with or without direct communication with the user. That is to say, the system can be configured to notify a remote authorized person that the system is in use, and to provide the remote authorized person with data regarding the eye examination process, such that the remote authorized person can provide input and if necessary take control of the system. This way, the system can be configured for a semi-automatic eye examination.

The system can be further configured to transmit the prescription and frame details to a remote lab which can include a central server configured to collect data from a plurality of remote system for ordering spectacles. The system can thus be a port, such as a booth disposed in public locations, such as malls, shopping center, hospitals etc., and can be connected to a central lab preparing the spectacles and sending same to the user's address.

The central server at the lab can be further coupled to a 3D printer, for custom preparation of the frame in accordance with the user's preferences.

According to an example the system can be configured for collecting data regarding frame preferences from a plurality of user together with the user's gender and age. The collected data can be used to provide users with information regarding ongoing trends with respect to the user's age and gender.

Those skilled in the art to which the presently disclosed subject matter pertains will readily appreciate that numerous changes, variations, and modifications can be made without departing from the scope of the invention, mutatis mutandis.

The invention claimed is:

1. A method for carrying out an eye examination on an examinee, the method comprising:

providing a display configured for displaying a visual stimulus;

forming a visual path between said display and at least one eye of the examinee;

displaying on said display a series of visual stimuli on randomized locations with respect to the display, each one of said visual stimuli having visual characteristics;

detecting reflexive eye response of said at least one eye in response to said displaying of said series of visual stimuli;

assessing vision acuity of said at least one eye in accordance with said reflexive eye response, said location, and said characteristics of said visual stimulus.

2. The method according to claim 1 further comprising determining initial preset values of said optical parameters.

3. The method according to claim 1 wherein said eye response is selected from a group including lens tension, pupil size, saccade and eye muscles movement.

4. The method according to claim 1 wherein said step of displaying said at least one visual stimulus in the series of visual stimuli is carried out after said eye response is below a predetermined threshold.

5. The method according to claim 1 further comprising providing at least one adjustable lens assembly and adjusting optical parameters of said adjustable lens assembly after said eye response are detected.

6. The method according to claim 5 further comprising a step of adjusting said optical parameters and displaying a visual stimulus after said step of adjusting said optical parameters after displaying a first visual stimulus in the series of visual stimuli and before displaying the next visual stimulus in the series of visual stimuli.

7. The method according to claim 6 further comprising repeatedly adjusting optical parameters of said adjustable lens assembly between displaying of said first visual stimulus and said next visual stimulus until said reflexive eye response is below a predetermined threshold, said optical parameters related to correction of at least one vision impairment of said at least one eye, and wherein said step of assessing vision of said at least one eye is in accordance with values of said optical parameters when said reflexive eye response reach said threshold.

8. The method according to claim 5 wherein said optical parameters is spherical power.

9. The method according to claim 5 wherein said optical parameters is cylindrical power.

10. The method according to claim 9 wherein said optical parameters further includes cylindrical axis and wherein said visual stimulus includes an orientation having an axis, and wherein said step of displaying visual stimulus includes displaying said visual stimulus at various orientations and said step of assessing vision includes assessing the axis of said orientation of a visual stimulus for which eye responses were detected.

11. The method according to claim 1 wherein characteristics of said visual stimulus include detectability level.

12. The method according to claim 11 wherein said step of displaying visual stimulus in the series of visual stimuli includes displaying said visual stimulus in varying detectability level and wherein said step of assessing vision includes assessing the detectability level at which said eye response was detected.

13. The method according to claim 11 wherein said detectability level includes contrast of said visual stimulus with respect to background on said display.

14. The method according to claim 13 wherein said step of displaying at least one visual stimulus includes repeatedly adjusting contrast of said visual stimulus until said eye saccade is detected.

15. The method according to claim 14 wherein said step of assessing vision includes assessing the contrast at which said eye response was detected for each of said visual stimuli.

16. The method according to claim 15 wherein said visual stimulus includes at least one line and wherein said orientation is an angle of said line with respect to the horizon and wherein said series of stimuli includes visual stimulus having at least one angle with respect to the horizon, wherein said angle varies between 0°-180°.

17. The method according to claim 15 wherein said step of assessing vision includes performing nonlinear regression analysis in which data related to said contrast is modeled by a function characterizing vision impairments and wherein said function is modeled by calculation of least mean squares of said contrasts for each of said angles.

18. The method according to claim 13 wherein said step of detecting includes detecting saccade of said eye towards said randomized location and wherein each one of said visual stimuli in the a series of visual stimuli has an orientation, and wherein said step of assessing vision includes assessing the contrast at which said eye response was detected for each of said visual stimuli.

19. The method according to claim 11 wherein said detectability level includes spatial frequency of elements of said visual stimulus.

20. The method according to claim 11 wherein said step of detecting reflexive eye response includes detecting eye saccade towards said visual stimulus.

* * * * *